US008926171B2

(12) United States Patent
Danley et al.

(10) Patent No.: US 8,926,171 B2
(45) Date of Patent: Jan. 6, 2015

(54) SIMULTANEOUS DIFFERENTIAL THERMAL ANALYSIS SYSTEM

(75) Inventors: Robert L. Danley, Collingswood, NJ (US); Xiaoping Hu, New Castle, DE (US)

(73) Assignee: Waters Technologies Corporation, Milford, MA (US)

( * ) Notice: Subject to any disclaimer, the term of this patent is extended or adjusted under 35 U.S.C. 154(b) by 691 days.

(21) Appl. No.: 12/766,971

(22) Filed: Apr. 26, 2010

(65) Prior Publication Data

US 2010/0278210 A1    Nov. 4, 2010

Related U.S. Application Data

(60) Provisional application No. 61/173,764, filed on Apr. 29, 2009.

(51) Int. Cl.
| | |
|---|---|
| *G01N 25/00* | (2006.01) |
| *G01K 17/00* | (2006.01) |
| *G01K 1/00* | (2006.01) |
| *G01G 21/07* | (2006.01) |
| *G01G 21/22* | (2006.01) |
| *G01G 21/16* | (2006.01) |
| *G01N 5/04* | (2006.01) |
| *G01G 21/23* | (2006.01) |

(52) U.S. Cl.
CPC .............. *G01G 21/07* (2013.01); *G01G 21/22* (2013.01); *G01G 21/16* (2013.01); *G01G 21/23* (2013.01); *G01N 5/04* (2013.01)
USPC .................. 374/14; 374/12; 374/33; 374/208

(58) Field of Classification Search
USPC ........................................ 374/33, 12, 14, 208
See application file for complete search history.

(56) References Cited

U.S. PATENT DOCUMENTS

| | | | |
|---|---|---|---|
| 3,685,604 | A | 8/1972 | Smith et al. |
| 5,826,983 | A | 10/1998 | Nakamura et al. |
| 6,057,516 | A | 5/2000 | Nakamura et al. |
| 6,232,567 | B1 | 5/2001 | Bonino et al. |
| 7,619,170 | B2 | 11/2009 | Burkhard et al. |
| 2005/0045388 | A1* | 3/2005 | Burkhard ...................... 177/187 |

(Continued)

FOREIGN PATENT DOCUMENTS

| | | |
|---|---|---|
| EP | 1925920 | 5/2008 |
| JP | 08129015 | 5/2008 |

(Continued)

OTHER PUBLICATIONS

PCT International Search Report for PCT/US2010/032669, dated Aug. 4, 2000, 3 pages.

(Continued)

*Primary Examiner* — Mirellys Jagan
(74) *Attorney, Agent, or Firm* — Waters Technologies Corporation

(57) ABSTRACT

A balance for a simultaneous differential thermal analysis instrument that combines gravimetric measurements with measurements that require propagation of electrical signals from the sample holder to an apparatus for recording the electrical signals. In one embodiment of the present invention, conductive cross-flexure pivots are used in a parallel guided balance to mechanically and electrically couple the components of the balance mechanism to the apparatus that records the electrical signals.

27 Claims, 5 Drawing Sheets

(56) References Cited

U.S. PATENT DOCUMENTS

| | | | |
|---|---|---|---|
| 2006/0266562 A1* | 11/2006 | Genoud et al. | 177/212 |
| 2008/0121048 A1 | 5/2008 | Burkhard et al. | |
| 2008/0144694 A1 | 6/2008 | Danley et al. | |
| 2010/0278209 A1* | 11/2010 | Danley et al. | 374/10 |

FOREIGN PATENT DOCUMENTS

| | | |
|---|---|---|
| WO | 2008145426 | 12/2008 |
| WO | PCT/ISA/210 | 7/2010 |
| WO | PCT/ISA/237 | 7/2010 |

OTHER PUBLICATIONS

PCT International Written Opinion Report for PCT/US2010/032669, dated Aug. 4, 2000, 6 pages.
Translation of Notice of Rejection for Japanese Patent Application No. 2012-508618, mailing date of Feb. 10, 2014, 5 pages.
Translation of Notice of Rejection for Japanese Patent Application No. 2012-508621, mailing date of Feb. 10, 2014, 5 pages.
Extended European Search Report for European Patent Application No. 10770230.0, mailing date of Oct. 4, 2013, 7 pages.
Extended European Search Report for European Patent Application No. 10770232.6, mailing date of Oct. 4, 2013, 8 pages.

* cited by examiner

SIMULTANEOUS DIFFERENTIAL THERMAL ANALYSIS SYSTEM

RELATED APPLICATIONS

This application claims priority to Provisional Application No. 61/173,764, filed Apr. 29, 2009, which is incorporated by reference in its entirety. Concurrently filed application entitled "Simultaneous Differential Thermal Analysis System," U.S. patent application Ser. No. 12/766,964, listing Robert L. Danley and Xiaoping Hu as the inventors, is also incorporated in its entirety.

BACKGROUND

1. Field of the Invention

The present invention is related to apparatus for measuring thermal properties of samples of materials.

2. Background of the Invention

A simultaneous thermal or differential thermal analyzer (SDT) comprises a combination of a thermogravimetric analyzer, TGA (also known as a thermobalance), and either a differential thermal analyzer (DTA) or a differential scanning calorimeter (DSC). Thus, the instrument allows a user to simultaneously measure mass changes and to monitor a signal based on sensible or latent heat changes in the sample.

Thus, an SDT allows a user to measure both the heat flows (DSC or DTA) and weight changes (TGA) associated with transitions in a material as a function of temperature and time in a controlled atmosphere. Simultaneous measurement of these key material properties not only improves productivity but also simplifies interpretation of results. The complementary information obtained allows differentiation between endothermic and exothermic events which have no associated weight loss (e.g. melting and crystallization) and those which involve a weight loss (e.g. degradation). The combined evaluation also assures identical experimental and sampling conditions for both measurements, thereby eliminating those sources of uncertainty. Simultaneous DSC-TGA covers a wide temperature range from below ambient to above 1500° C., making it a powerful tool for studying a wide variety of materials including organic materials, notably polymers, and ceramics, metals, and other inorganics.

Typically, the design of such an SDT instrument comprises a combination of an existing microbalance component with a DTA or DSC measuring component. In fact, early SDT instruments were based on existing laboratory balances.

Generally, there are two types of microbalances in common use in SDT and TGA instruments, both of which employ the null balance principle, in which a restoring force is applied to the balance structure to maintain the balance in equilibrium. The restoring force, which is proportional to the change in weight, is the measured quantity in each type of microbalance. In both cases, the restoring force is applied electromagnetically as a response to a displacement of the balance structure, which is typically detected by optical means. Using such a balance, a very high degree of mass sensitivity and a very high resolution of changes in mass are readily obtained.

A first type of balance is the dual arm meter movement balance, in which a d'Arsonval meter movement (also referred to herein as a "meter movement balance") supports the balance beam and applies the restoring force as a torque.

In an SDT instrument that employs a d'Arsonval meter (also termed "meter movement"), when the sample weight in a sample holder connected to the balance changes during an experiment, a displacement sensor near the TGA balance senses movement of the balance away from the equilibrium position and electric circuitry generates the current necessary to restore the balance to equilibrium.

The second type of balance used in SDT and TGA instruments is the guided balance, in which the weighed mass is supported by a mechanism that constrains the movement of the weighed mass. Typically, the guided balance mechanism comprises a parallel four-bar linkage with elastic flexure pivots. This mechanism is termed a parallel guided balance. An electromagnetic actuator is used to apply a restoring force to the linkage, while a displacement sensor detects movement away from the equilibrium position and electric circuitry generates any current necessary to restore the balance to equilibrium.

SDT and TGA instruments may be classified as horizontal or vertical instruments based on the orientation of the heating furnace and the relative position of the balance. In principle, the measurement of weight may be perturbed by thermal expansion of the structure that extends into the furnace, and by forces exerted by movement of gas in the furnace caused by the action of purging the furnace or by buoyancy induced flows, in addition to buoyancy forces resulting from gas density changes. The magnitude of these weighing errors depends upon the configuration of the SDT instrument. In a horizontal furnace, thermal expansion of the beams that extend into the furnace may cause large weighing errors, while a vertical furnace configuration is largely immune to these effects, because thermal expansion occurs parallel to the Earth's gravitational field. On the other hand, vertical instruments are far more susceptible to fluid forces because thermal gradients in the furnace are parallel to the direction of the gravitational field which favors buoyancy driven flows and because the movement of the balance mechanism is parallel to the direction of purge gas flow. Horizontal instruments are largely immune to these forces because temperature gradients in the furnace are orthogonal to the gravitational field which is unfavorable to buoyancy driven flows and the movement of the balance mechanism is orthogonal to the direction of purge gas flow. Finally, buoyancy forces due to gas density changes may affect both horizontal and vertical furnace configurations to a similar degree.

As noted above, an SDT instrument combines a TGA measurement with a DTA or DSC type measurement, which requires that at least the sample side of the heat flow rate sensing device be supported by the balance mechanism. During sample measurement, a sample can be heated or cooled to examine changes in the sample induced by changes in temperature. In the case of sample heating, the heating takes place while at least a portion of the member supporting the sample extends into a furnace used to heat the sample. As the sample is heated, mass changes in the sample cause the balance mechanism to deflect from equilibrium, such that the restoring force needed to maintain the equilibrium can be measured. At the same time, a thermal signal (either DTA or DSC) is transmitted using wires that extend from the sample region to the stationary or fixed part of the instrument, so that analysis of the material changes taking place can be performed based upon the thermal signals received from the sample. Thus, the wires that carry the DSC or DTA signals from the sample region must connect the moving part of the balance to the fixed part. These signal wires typically exert a parasitic force on the balance that constitutes a weighing error.

Several factors can lead to the result wherein the wires contribute to weighing errors in SDT measurements. In principle, the forces exerted by the wires on the balance need not result in weighing errors, as long as the response in the wires to a displacement is linearly elastic. In other words, if the forces the wires exert are strictly linearly proportional to the displacement of the wires and the proportionality constant does not change, weighing errors caused by the wires could be avoided. If the response of the wires is not linearly elastic, weighing errors will result. Because the wires are usually deformed during installation in the SDT apparatus, the wires will almost always exert some force on the balance regardless of the balance position or whether any motion is taking place. No force would be exerted by the wires on the balance only if they were in their undeformed position. Another problem that may arise is that the wires may relax over time, resulting in changes in the force exerted by the wires. Typically, the wires are bent to the required shape when they are installed in the SDT apparatus, such that the deformation of the wires is at least partially plastic in nature. Over time, some of the plastic strain relaxes, thus changing the force exerted by the wire in a static position, as well as the force resulting from a displacement of the balance. In principle, the wires can be annealed or stress relieved, but given that they are generally fine and easily bent, it is difficult to handle and install the wires without deforming them.

In addition to wires, pivot structures that are necessary to connect fixed parts of a balance to moving parts of the balance, or that connect two moving parts of a balance, can introduce forces that may influence the measurement of sample weight.

Of the two types of balance, the meter movement type, given its lower mass and lower stiffness, is more sensitive and has faster dynamic response. The guided balance is more robust and is immune to the thermal expansion effects described above when used in a horizontal configuration. The guided balance-type SDT instrument may be used in conjunction with either the vertical or horizontal furnace configuration. Generally, the meter movement balance is used with the horizontal furnace configuration.

In the horizontal configuration, the meter movement balance is typically employed in a differential weighing configuration in which two balances, a sample and a reference balance, are operated in parallel. One balance weighs the sample and its container, while the other balance weighs an empty container or an inert reference sample in the container. Subtracting the reference weight measurement from the sample weight measurement eliminates the weighing error due to thermal expansion of the weighing structure and the weighing error due to buoyancy forces acting on the apparatus. Sample buoyancy forces are still a potential source of error in the dual balance configuration. Since the dual balance configuration employs a horizontal furnace configuration, the balances are isolated from forces arising from fluid motion, whether due to purge gas flow or to buoyancy differences resulting from temperature variations in the furnace, because these forces act orthogonally to the gravitational field.

In a dual balance meter movement type SDT (also termed "dual balance SDT" hereinafter) each of the sample and reference balances includes a meter movement component, optical displacement sensor and electronics to maintain the respective balance in the equilibrium position. Besides incurring undesirable cost because of duplication of components, a dual balance SDT system suffers from potential mismatches between the components of the two balance assemblies, such as in the meter movements. Another shortcoming of this design is that the meter movement components (or "meter movements") must support the entire weight of the balance beam and DTA or DSC holder structure.

D'Arsonval meter movements may be made with either jewel bearings or a thin taut band supporting the rotating part of the meter. Generally, taut band suspensions are preferred because they operate without friction. Displacement of the moving part of the meter twists the taut band slightly. Elastic deflection of the taut band is very linear and highly repeatable, whereas friction in jewel bearings is far more nonlinear and far less repeatable. On the other hand, jewel bearing meter movements can support much larger loads than those supported by taut band suspensions. Because a taut band suspension must support the entire weight of the beam, the sample (or reference) holder, DTA or DSC sensor, and sample, the weighing capacity is limited to a small fraction of the capacity of the taut band, most of which is used to support the beam, holder, and sensor. Thus, the taut band instruments tend to have low weighing capacity.

In view of the above, it will be appreciated that further improvement of balance apparatus in SDT instruments is needed.

SUMMARY OF THE INVENTION

In a preferred embodiment of the invention, an improved SDT configuration includes a parallel guided balance structure that contains one or more members constructed from insulating material such as printed circuit board material (PCB). The PCB members are configured both to act as structural components of the balance and to conduct a sensor signal from a sample or reference temperature sensor used in a DTA or DSC measurement.

In one aspect of the invention, an SDT balance comprises a plurality of PCB members that act as structural components and include conductors that run along the surface of the structural components and/or within the structural components so as to conduct electrical signals from sensor elements located in sample and reference holders. In one aspect of the invention, a continuous conductive path is formed that leads from a first PCB member to a second, adjacent PCB member, wherein the first and the second PCB member are mutually connected by a conductive flexure pivot.

In a preferred embodiment of the invention, one or more pivots of the PCB-based SDT apparatus are configured using a crossed-flexure design, and are constructed so that the crossed flexures can carry the DTA or DSC signals between components of the balance structure. In other words, the cross flexures serve two separate functions: they provide 1) a conductive link between adjacent PCB members or between a PCB member and another structural member of the SDT apparatus, and 2) a pivoting means that allows the adjacent PCB members or PCB member and other structural member to pivot about one another.

In accordance with the present invention, a crossed-flexure pivot comprises a crossed pair of electrically conductive flexible members and an abutment structure. The abutment structure comprises two pairs of abutments wherein a first pair of abutments is configured to attach to respective ends of a first flexible member and a second pair of abutments is configured to attach to respective ends of a second flexible member that crosses the first flexible member.

For example, the crossed-flexure pivots can be soldered directly to conductive traces on the printed circuit board material. In this way, a continuous electrical path is formed between conductors on a first PCB and conductors on an adjacent PCB. The continuous electrical path runs from the conductor on the first PCB through a first abutment affixed to the first PCB, through a first cross-flexure member attached in a first region to the first abutment, through a second abutment attached to the crossed-flexure member in a second region, and into a second conductor connected to the second abutment on an adjacent PCB.

In an embodiment of the present invention, the crossed-flexure pivots are mechanically fastened to conductive traces on the printed circuit board material. In this embodiment a continuous electrical path is formed between conductors on a first PCB and conductors on an adjacent PCB. The continuous electrical path runs from the conductor on the first PCB through a first abutment affixed to the first PCB, through a first cross-flexure member attached in a first region to the first abutment, through a second abutment attached to the crossed-flexure member in a second region, and into a second conductor connected to the second abutment on an adjacent PCB.

In one variant of the present invention, the abutment structure of a cross-flexure pivot in an SDT apparatus comprises a conductive sheet material such as sheet metal, including copper (e.g., oxygen-free copper) or other metal. In one configuration, an abutment comprises a generally L-shaped structure in which a first leg of the "L" is affixed to a surface of a structural member, such as a PCB, and a second leg of the "L" extends outwardly from the surface of the structural member. In one embodiment of the invention, the second leg of the "L" of an abutment is folded on itself so as to form a slot region that accommodates an end portion of a flat flexible member.

In accordance with an embodiment of the present invention, the pair of flat flexible members forms a substantially orthogonal cross when the SDT apparatus is in an equilibrium position for weighing. Each flat flexible member may comprise a thin planar conductive strip in which the plane of the strip is substantially orthogonal to the plane of the PCB member.

In accordance with an embodiment of the present invention, the abutments comprise a sheet metal material, such as copper (e.g., oxygen-free copper), that is configured for easy soldering to conductive traces located on the PCB.

In accordance with embodiments of the present invention, an SDT instrument comprises a PCB/cross flexure pivot design in which adjacent structural members comprise two different PCB members or a PCB member and a non-PCB member that are electrically and mechanically coupled using a cross-flexure pivot. The SDT instrument comprises a parallel guided balance.

In accordance with an embodiment of the present invention, to avoid extraneous the thermoelectric voltages that could be generated where different materials are in contact, for instance where the flex pivots are soldered to the PCB material, the balance structure is housed in an enclosure that is maintained at a constant uniform temperature. The beams used to support the sample holders attach to the balance structure within the constant temperature enclosure.

In accordance with embodiments of the present invention, the sample holders, including thermocouples for the DTA or DSC measurement, are made of high temperature resistant materials, such as high purity ceramics and platinum alloys. In accordance with an embodiment of the invention, a parallel guided balance SDT apparatus comprises a four-bar parallel linkage that supports and guides a single structural member that supports sample and reference holders and associated DTA or DSC sensors. The linkage comprises a fixed vertical member that is joined to two equal length horizontal members by a first set of crossed flexure pivots, wherein the cross-flexure pivots are capable of transmitting DTA or DSC sensor signals between the fixed vertical member and horizontal members. A second vertical member of equal length to the fixed vertical member is joined to the opposite ends of the horizontal members by a second set of crossed flexure pivots. The second vertical member is thus constrained to move such that the second vertical member remains oriented parallel to the fixed member and in approximately a straight line as long as the displacements are small and the horizontal members remain close to the horizontal position.

In accordance with an embodiment of the present invention, a component is provided to support the DTA or DSC sensor and sample and reference holders, wherein the component is attached to the movable member. In an embodiment of the present invention, at least the two horizontal members of the linkage are constructed of PCB material to which the first and second set of crossed-flexure pivots are attached, enabling the DSC or DTA signals to be carried from the moving portion of the balance to the fixed part of the balance without the need for flexible temperature sensor lead wires, thus avoiding the parasitic forces associated with such lead wires. In accordance with alternative embodiments of the present invention, a parallel-guided balance having a first and second set of cross-flexure pivots that join a horizontal member to a fixed vertical member and movable vertical member, respectively, is adapted for use with a vertical furnace or a horizontal furnace configuration.

BRIEF DESCRIPTION OF THE DRAWINGS

FIG. 1a shows in perspective view a prior art configuration of a measurement apparatus portion of an SDT using a meter movement balance.

FIG. 1b shows a close up of a sample holder of the apparatus of FIG. 1a.

DETAILED DESCRIPTION

The present invention provides novel and inventive arrangements of components that can be used in apparatus that combine simultaneous gravimetric measurements of a sample with measurements of the sample that require propagation of electrical signals from the sample area to an apparatus for recording the electrical signals. For example, embodiments of the present invention provide improved configurations of sample measurement balances that can be used in conjunction with thermal measurements in an SDT instrument.

As described above, SDT instruments perform simultaneous gravimetric measurements and thermal measurements, such as DSC or DTA. An SDT apparatus can simultaneously measure changes in a plurality of sample properties that take place during heating, such as changes in weight, phase changes, and the like.

Figure 1:
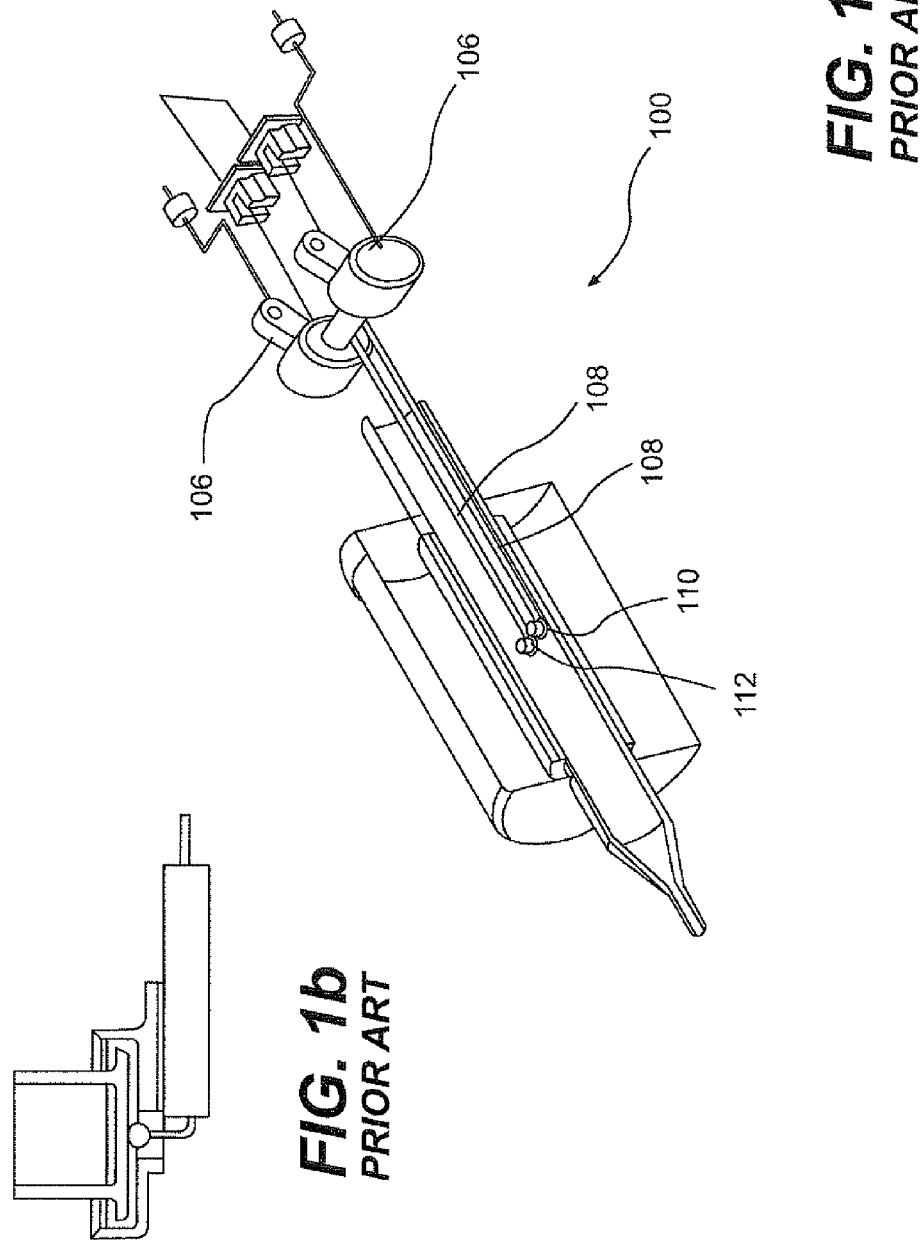

FIGS. 1a and 1b depict a known configuration of a measurement apparatus portion 100 of an SDT apparatus, in this case, a meter movement balance SDT. Apparatus 100 includes hardware for performing simultaneous thermal measurements (e.g., DSC or DTA) and gravimetric measurements of a sample placed in sample holder 112. The term "thermal measurements," as used herein, refers to measurements that use a thermocouple or other temperature-measuring device that is located at or near a sample or a reference holder. The thermal measurements can be, for example, measurements for sensing heat flow rate, as in known DSC/DTA sensors. A hallmark of the thermal measurements is that an electrical signal propagates along conductors leading from the sample area and is detected and analyzed by components (not shown) that are external to measurement apparatus 100.

Apparatus 100 includes a differential horizontal balance that contains two meter movements 106 and accompanying sensors that are used to separately weigh samples and references placed in the sample and reference holders of respective sample and reference balance arms 108, Electrical signals are conducted from each thermocouple using wires that run from the sample or reference to an external point for detecting the electrical signals. In this apparatus, the electrical wires can exert a force on the balance arms that can interfere with accurate measurement of weight changes taking place in the sample. For example, a set of wires coupled to the sample holder may exert a different force on the sample balance arm than that exerted on the reference balance arm by wires coupled to the reference holder. In this manner, the differential change in weight between the sample and reference material that may occur as the sample is heated can be obscured by the parasitic effect of the force exerted by wires, which may be unpredictable and of unknown magnitude. Similarly, in parallel guided balances, wires coupled to the sample and reference holders, for example, at pivot points of balance arms, can degrade the accuracy of weight measurements.

In accordance with the present invention, an improved balance assembly is provided that is compatible for use in SDT apparatus in which an electrical signal is conducted from a sample holder that is coupled to the balance. In an embodiment of the present invention, a balance assembly includes one or more composite structural members (also termed "composite members" herein, which refers to the fact that the members may have an insulating part and a conductive part) that include an insulating portion and conductive portions, for example, conductive paths that are configured to conduct electrical signals from a sample or reference sensor. The structural members thus perform a mechanical function and may also perform an electrical function. For example, the structural members can be fabricated from printed circuit board material (PCB) or similar material, or another type of insulator material, such as glass, glass ceramic, or other material. A conductive material is disposed on and/or within the insulator. The conductive material can be plated metal, deposited metal, or similar known conductors that are used in printed circuit boards, for example.

In an embodiment of the invention, the composite member is used as a horizontal member of an SDT balance, such as a horizontal member of a parallel guided balance. In accordance with embodiments of the present invention, conductive paths disposed within and/or upon the surface of a composite member are used in place of wires to conduct electrical signals from sample and reference sensors.

In accordance with embodiments of the present invention, the composite members are configured to mechanically couple with the rest of a balance assembly so as to reduce any parasitic force acting on the balance in comparison to known SDT balances in which wires are used to transmit signals between adjacent components where a relative motion takes place between components. In one variant of the present invention, the mechanical coupling of a composite member to an adjacent member is facilitated using a pivot, such as a crossed-flexure pivot. The pivot is formed from a conductive material, such as a sheet metal and is configured to electrically couple conductive paths disposed on the composite member with conductors disposed in the adjacent component so as to form a continuous electrical path between the adjacent components that is not interrupted when the adjacent components are pivoted with respect to one another.

Figure 2:
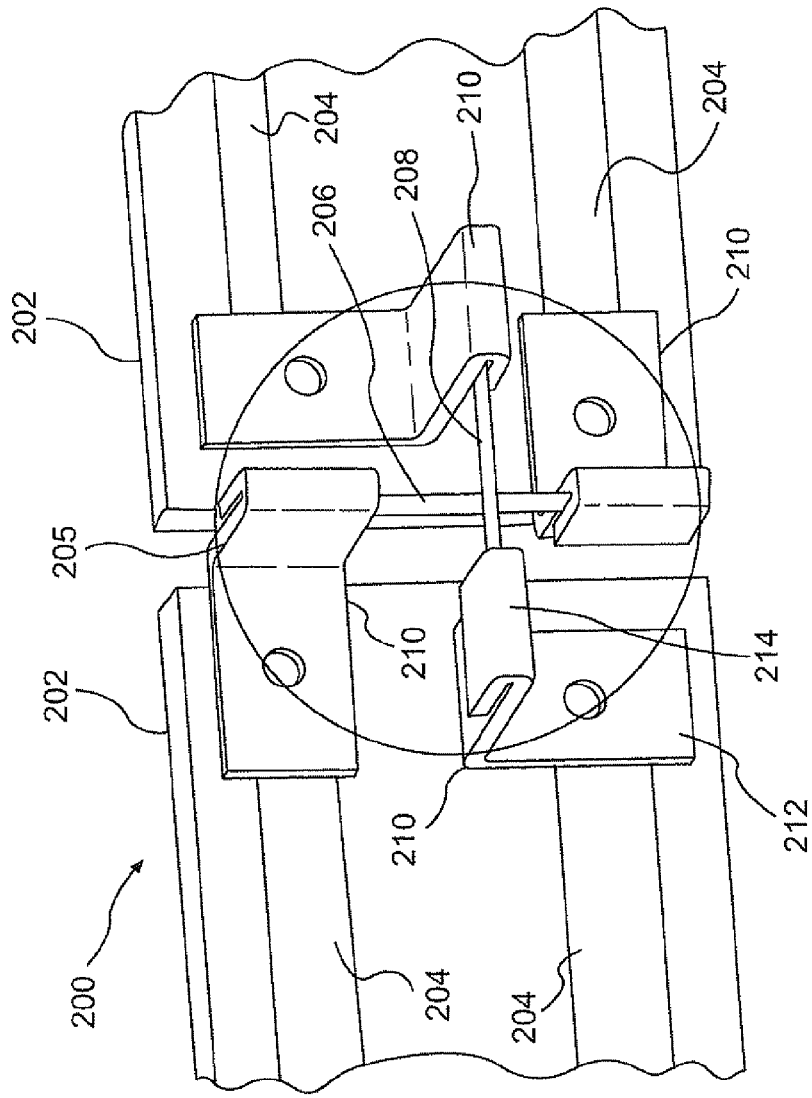
FIG. 2 depicts a portion of a balance having a crossed-flexure pivot to couple adjacent structural members, in accordance with an embodiment of the present invention.

FIG. 2 depicts a coupling assembly 200 of a balance in which a cross-flexure pivot is configured to mechanically and electrically couple adjacent composite members, in accordance with an embodiment of the present invention. The adjacent composite members 202 can be, for example, an insulating substrate that is provided with conductive paths (also termed "traces" herein) on its surface and/or within the substrate. Specifically, the composite members 202 can be PCB material that is provided with conductive paths 204. The composite member can also be formed using conductive traces formed upon and/or within another insulator, such as a ceramic, glass ceramic, and glass, among other materials.

In one embodiment of the invention, coupling assembly 200 is a pivot region in a horizontal balance arm. In the embodiment of the invention depicted in FIG. 2, adjacent composite members 202 are substantially flat structures typical of PCBs.

The adjacent composite members 202 each include two abutments 210 that, together with vertical flexure 206 and horizontal flexure 208, form a crossed-flexure pivot 205 that connects the adjacent composite members. In accordance with an embodiment of the present invention, abutments 210 are formed from a thin conductive material, such as sheet metal, for example, copper (e.g., oxygen-free copper) or another material that can easily be electrically coupled to conductive paths 204. In one example, abutments 210 are soldered to conductive paths 204. In accordance with alternative embodiments of the invention, the conductive traces 204 that are coupled to abutments 210 can be additionally configured to conduct signals from a DTA or DSC sensor, or can be used solely for the purposes of affixing the abutments to the body of the composite member 202.

In the example shown in FIG. 2, abutments 210 have an "L" shape. However, abutments 210 can also assume other shapes. Cross flexures 206, 208 each are thin conductive materials, such as sheet metal having high conductivity.

In accordance with embodiments of the present invention, coupling assembly 200 is configured to improve the performance of a measuring apparatus, such as an SDT apparatus. Composite members 202 are configured to provide sufficient mechanical rigidity and strength so as to act as structural members of a balance, as noted above. In addition, because the body of composite members 202 is electrically insulating, a plurality of conductive paths 204 that are electrically isolated from other paths can be formed on the composite members. Moreover, the cross-flexure pivot 205 provides a means for the mutually adjacent members 202 to pivot with respect to one another while simultaneously providing an electrically conductive connection between conductive paths on the adjacent composite members. This eliminates the need for electrically conductive wires to couple between the adjacent members. Accordingly, parasitic mechanical forces from wires that could act upon balance members are eliminated.

In the example shown in FIG. 2, adjacent composite members 202 are disposed substantially parallel to one another. In other embodiments of the present invention, a coupling assembly having a cross-flexure pivot could comprise adjacent composite members that are disposed at an angle to one another, for example, at a normal angle. In addition, one adjacent composite member can be a PCB board having electrical traces while the other adjacent composite member can be another insulator that supports conductive paths.

Figure 3:
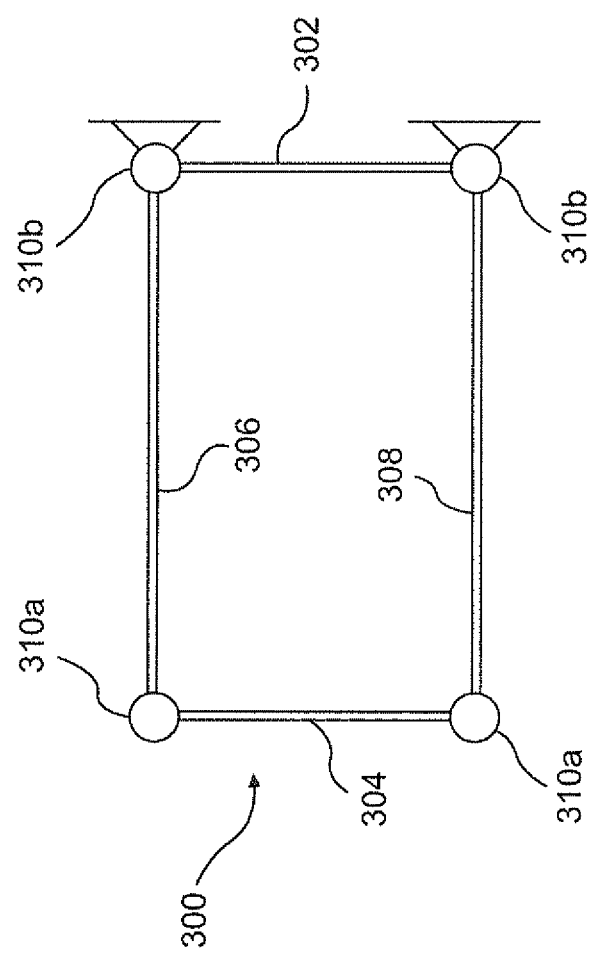
FIG. 3 depicts a side view of a parallel guided balance mechanism, arranged in accordance with an embodiment of the present invention.
Figure 4:
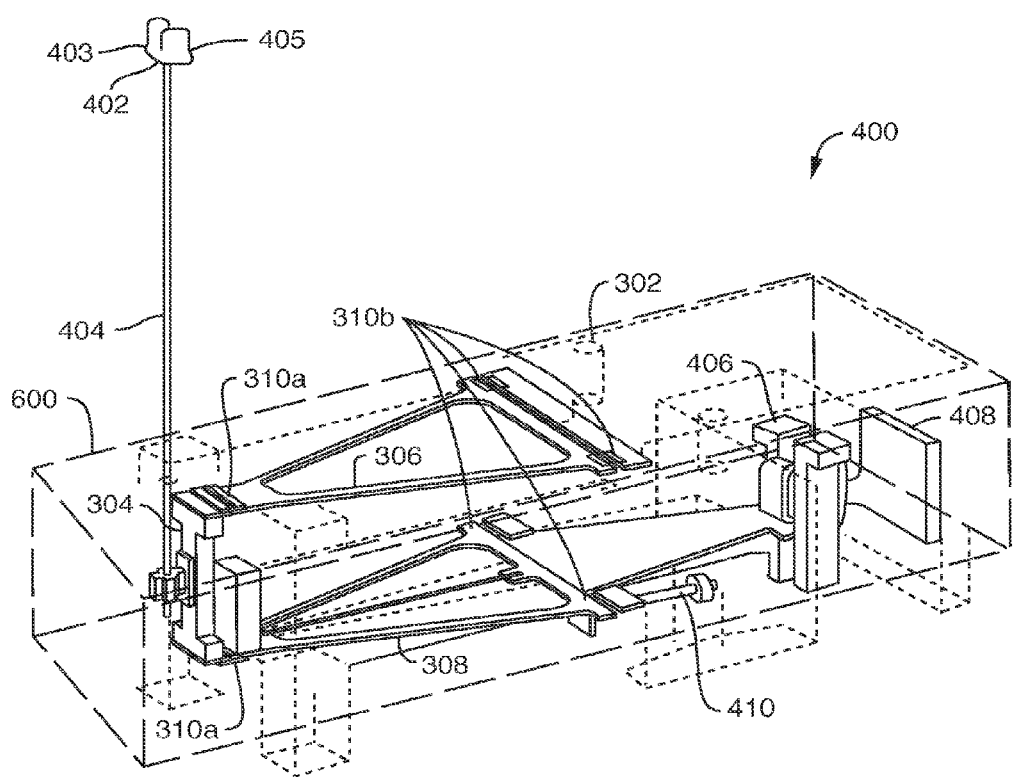
FIG. 4 depicts a perspective view of a parallel guided balance mechanism and thermal measurement arm of an SDT apparatus, arranged in accordance with an embodiment of the present invention

FIGS. 3 and 4 depict a side view and perspective view, respectively, of aspects of a parallel guided balance, in accordance with another embodiment of the present invention. Parallel 4-bar linkage 300 includes a fixed generally vertical member 302, an upper horizontal member 306, lower horizontal member 308, and movable vertical member 304. Each member is joined to its adjacent members through pivots 310a-310b. Upper and lower horizontal members 306 and 308 are substantially rigid and are each pivotally attached to fixed vertical member 302. As evident from the parallelogram arrangement depicted in FIG. 3, movable member 304 is constrained to move such that its orientation remains parallel to fixed vertical member 302.

In accordance with an embodiment of the present invention, one or more of the upper and lower horizontal members 306 and 308 is a composite structural member as described above. Preferably, members 306 and 308 comprise the same type of composite structural member and have matching thermal expansion coefficients to ensure thermal expansion matching of the upper and lower members. This avoids member 306 from having a different length than member 308, resulting in the linkage (members 302-308) assuming a trapezoidal shape during heating or cooling.

For example, both upper and lower horizontal members can be made of PCB material that includes electrically conductive paths for conducting electrical signals from holder assembly 402. As further depicted in FIG. 4, the upper and lower horizontal members have an open triangular shape. In accordance with embodiments of the present invention, wires (not shown) in vertical tube 404 are connected to sample and reference sensors in holder assembly 402. The wires are also connected to conductive paths (not shown) that are disposed on movable vertical member 304, which comprises, at least in part, an insulating portion that can support conductive paths without electrically shorting the conductive paths. The conductive paths of movable vertical member 304 are electrically coupled via one or more pivots 310a to electrically conductive paths (not shown) disposed in one or more of the upper and lower horizontal members 306, 308. For example, one or more of pivots 310a can be a crossed-flexure pivot whose operation is similar to that described above with respect to FIG. 2, except that the pivots 310a join adjacent members that are disposed at right angles to one another.

In addition, at least one of horizontal members 306, 308 is configured to electrically couple to fixed vertical member 302 to provide electrical signals that can be transmitted for display and/or analysis by external devices (not shown).

In the apparatus 400 depicted in FIG. 4 an apex of each of the triangular upper and lower horizontal members 306, 308 connects to the movable vertical member, thereby forming a pair of pivots 310a, while a base of each triangular horizontal member is connected to fixed vertical member 302 (shown in phantom) through two pivots 310b each. Accordingly, not each one of pivots 310b is required to provide electrical coupling between horizontal members 306, and 308 and fixed vertical member 302. Fixed vertical member 302 is essentially the stationary apparatus towards the right of FIG. 4, to which the upper and lower horizontal members 306 and 308 are attached.

In operation, apparatus 400 is positioned such that holder 402 is located within a furnace (not shown). As the sample and reference holder temperatures change, resultant changes in the sample can result in changes in mass (weight) of the sample. For example, the sample could lose mass by decomposition or could gain mass by, for example, reacting with ambient gas, such that an oxide or nitride is formed depending on the composition of the ambient gas. Because sample tube 404 that supports holder 402 is rigidly coupled to movable member 304, changes in mass of the sample holder/sample combination cause a deflection in the position of movable member 304, which is detected at position sensor 408. This positional change can then be compensated for using linear motor 406, and the sample mass change subsequently calculated based upon the force used to restore the position of movable member 304.

At the same time as movable vertical member 304 moves in an upward and/or downward direction, electrical signals from sensors in sample and reference holders 403 and 405, respectively, in holder assembly 402 are conducted from holder assembly 402 to electronics (not shown) in order to calculate, for example, changes in heat flow to the sample. The electrical signals are conducted along a conductive path that includes one or more pivots 310a and 310b, as well as conductive paths formed in one or more of composite horizontal members 306 and 308. Accordingly, the electrical signals are conducted without the use of wires in the regions of pivots 310a and 310b, thereby removing any parasitic force due to wires that can alter the measurement of sample mass changes.

FIG. 4 depicts an exemplary instrument design in which sample holder 404 is configured for use in a vertical furnace. In other embodiments of the present invention, sample holder 404 can extend from movable member 304 in a horizontal direction for use in a horizontal furnace.

Figure 5:
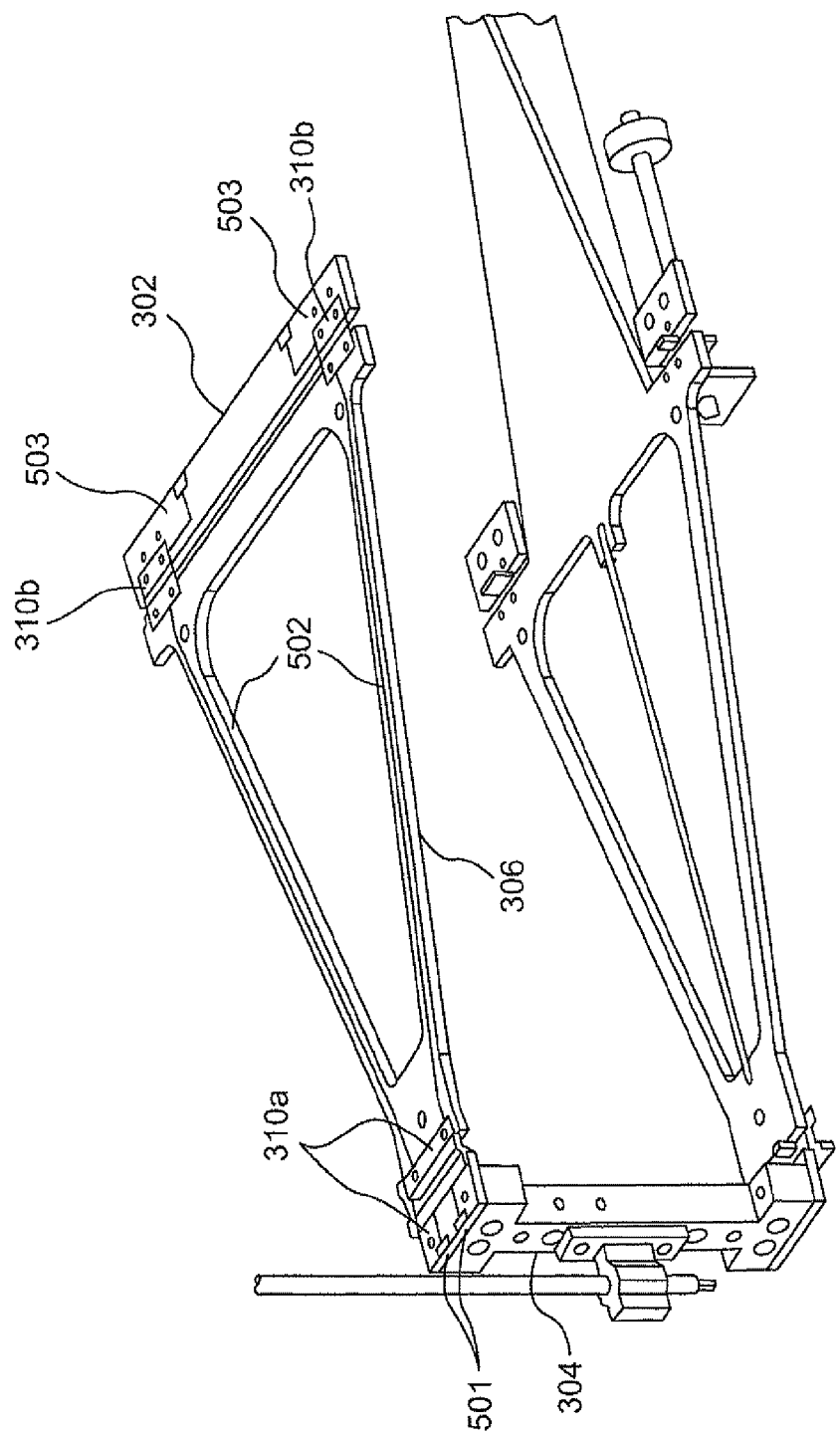
FIG. 5 is an enlarged view of a portion of the parallel guided balance shown in FIG. 4, illustrating conductive traces on the upper horizontal member.

FIG. 5 shows an enlarged portion of the parallel-guided balance mechanism of FIG. 4. Flexures 310 join triangular upper horizontal member 306 to moving vertical member 304 at the apex of the triangular member and to fixed vertical member 302 along the base of the triangle. Conductive traces 501 on moving member 304 are connected at one end to the signal wires (not shown) of the temperature sensor in the sample and reference holder and at the other end to the abutments of flexures 310. The abutments at the opposite end of flexures 310 are in turn attached to traces 502 that run along the surface of the long sides of upper triangular member 306. Traces 502 in turn attach to the abutments of flexures 310 at the base of the triangular member. The abutments on the opposite ends of the flexures 310 are attached to traces 503 on the surface of fixed member 302. Thus, electrical signals from the temperature sensor are transmitted from the sensor lead wires via conductive traces 501 on moving member 304, flexures 310, and conductive traces 502 on triangular upper horizontal member 306 to conductive traces 503 on the fixed member 302. Conductive traces 503 are in turn attached to signal wires (not shown) that transmit the temperature signal to the measurement electronics (not shown). In a similar manner, additional conductive traces may be added to moving member 304, upper triangular member 306, lower triangular member 308 and fixed member 302. The conductive traces can be joined by flexures. In this manner, one, two or more temperature signals used in the measurement of sample temperature or heat flow rate may be transmitted from the moving to the stationary parts of parallel-guided balances used in an SDT or TGA without the need for connecting wires. Although FIG. 5 shows the conductive traces on the upper horizontal member, as noted above they could also be disposed on the lower horizontal member or on both the upper and the lower horizontal members.

Given that the electrical signal path from the temperature sensor passes through materials of differential composition from the connection point of the sensor wires to the stationary members, the possibility of generation of extraneous thermoelectric voltages exists. These thermoelectric voltages would appear as a temperature measurement error on both the sample and reference temperature signals and may be essentially eliminated by ensuring that the interconnection system is isothermal. The interconnection system includes: the ends of the signal wires, their connection to the conductive traces on the movable member, the conductive traces on both of the horizontal members and the conductive traces on the stationary members, the flexures including abutments and flexible members and the ends of the copper wires that connect to the conductive traces on the stationary members. The copper wires carry the sample and reference temperature signals to the measurement electronics. To ensure that the interconnection system is isothermal, thick plates 600 of high thermal conductivity material (typically copper or oxygen-free copper, but silver, aluminum or other high thermal conductivity materials could also be used), surround and enclose the movable member and its conductive traces, the horizontal members and their conductive traces, the stationary members and their conductive traces, the flexure assemblies and their attachments, the ends of the temperature sensor signal wires where they connect to the conductive traces on the movable member and the ends of the copper signal wires where they connect to the conductive traces on the stationary members e.g., as shown in FIG. 4. Further, the entire balance assembly, including the isothermal plates and the interconnection system they enclose and the linear motor are housed within an enclosure whose temperature is precisely regulated at a temperature above ambient to ensure that everything within the enclosure remains at the constant temperature. This improves the temperature uniformity and stability of the isothermal plates and the temperature signal interconnect system they enclose, further ensuring that extraneous thermoelectric voltages do not create temperature errors in the sample and reference temperature sensor signals. In the case where the temperature sensors in the sample and reference holders are thermocouples, the reference junction temperature sensor is installed in one of the isothermal plates, ensuring that the reference temperature sensor is at the same temperature as the plates. Additionally, this ensures that the magnet within the linear motor remains at constant temperature so that the magnetic field it creates remains constant. Changes in the magnet temperature cause the field generated by the magnet to change, changing the proportionality of meter coil current to measured mass, introducing weight errors.

In summary, embodiments of the present invention present novel and improved configurations for performing simultaneous thermogravimetric and DSC or DTA type measurements (which require conducting electrical signals from sensors in the sample holder). In accordance with embodiments of the present invention, composite members of a balance that serve both as mechanical members and as means to conduct electrical signals from the sample/reference holders are substituted for conventional balance members that serve only a mechanical function. A crossed-flexure pivot configuration is provided in conjunction with one or more composite members, which configuration serves to eliminate the need for wires at a junction between members that are movable with respect to one another. One or more aspects of the composite member/crossed-flexure pivot configurations can be incorporated into a parallel guided balance.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A balance, comprising:
   a fixed vertical member pivotally adjoined to an upper horizontal member which is pivotally adjoined to a movable vertical member, which is pivotally adjoined to a lower horizontal member, which in turn is pivotally adjoined to the fixed vertical member, wherein the movable vertical member is constrained to move such that it remains parallel to the fixed vertical member and wherein the upper horizontal member and the lower horizontal member have matching coefficients of thermal expansion and matching lengths;
   plates of a high thermal conductivity material surrounding the movable vertical member, the upper horizontal member and the lower horizontal member;
   an electrically conductive path formed on one of the upper and lower horizontal members;
   an electrically conductive path formed on the movable vertical member;
   a first conductive flexure electrically connecting the electrically conductive path on the one horizontal member to the electrically conductive path on the movable vertical member, wherein the first conductive flexure pivotally connects the one horizontal member to the movable vertical member;
   a second conductive flexure pivotally connecting the one horizontal member to the fixed vertical member, and electrically connecting the electrically conductive path on the one horizontal member to conductive traces or wires affixed to the fixed vertical member;
   wherein the entire balance is housed within an enclosure that is maintained at a constant uniform temperature.

2. The balance of claim 1, wherein the upper and lower horizontal members are substantially rigid.

3. The balance of claim 1, comprising a sample holder rigidly coupled to the movable vertical member, a position sensor for detecting the deflection of the movable vertical member, and a linear motor, wherein the sample mass may be calculated based upon the force exerted by the linear motor required to restore the position of the movable vertical member.

4. The balance of claim 1, wherein one or more of the horizontal and vertical members is formed from printed circuit board material.

5. The balance of claim 1, wherein the horizontal members and the movable vertical member are components of a parallel guided balance.

6. The balance of claim 1, wherein a continuous electrical path runs from the electrically conductive path on the one horizontal member through a first abutment attached to the one horizontal member, through the first conductive flexure and through a second abutment to the first electrically conductive path on the movable vertical member.

7. The balance of claim 6, wherein the continuous electrical path runs from the electrically conductive path on the one horizontal member through a third abutment attached to the one horizontal member, through the second conductive flexure and through a fourth abutment to the electrically conductive path or the wires attached to the fixed vertical member.

8. A simultaneous differential thermal analysis instrument, comprising:
    a holder assembly that includes sample and reference sensors that are configured for one of DSC and DTA measurements;
    a first balance member mechanically coupled to the holder assembly;
    a second balance member pivotally connected to the first balance member using a crossed-flexure pivot; and
    plates of a high thermal conductivity material surrounding the first and second balance members,
    wherein each of the first and second balance members is a composite member that includes electrically conductive paths that are affixed to an insulating portion of the balance member, and
    wherein the instrument is configured to conduct electrical signals along an electrically conductive path that extends from the sample and/or reference holder assembly along at least a portion of the first balance member, through the pivot assembly and along at least a portion of the second balance member;
    wherein the instrument is housed within an enclosure that is maintained at a constant uniform temperature such that the instrument remains at a uniform temperature, thereby reducing extraneous thermoelectric voltages generated along the electrically conductive path.

9. The instrument of claim 8, wherein the crossed-flexure pivot comprises a first and a second flexure,
    wherein each flexure is connected on opposite ends to one abutment disposed on the first balance member and to another abutment disposed on the second balance member, and
    wherein each of the abutments is electrically connected to one of the conductive paths affixed to the first and second balance members.

10. The instrument of claim 8, wherein the first and second balance members each comprise a substantially flat planar surface, and
    wherein an angle between surfaces of planes that define the first and second balance members is one of about zero degrees and about ninety degrees.

11. The instrument of claim 8, wherein at least one of the first and second balance members comprises a printed circuit board material.

12. The instrument of claim 11, comprising conductive metal traces forming the electrically conductive paths on the balance members.

13. A parallel guided balance for use in a simultaneous differential thermal analysis instrument, comprising:
    a vertical fixed member;
    a first horizontal member pivotally connected to the vertical fixed member via a first set of pivots;
    a second horizontal member pivotally connected to the vertical fixed member via a second set of pivots;
    a movable vertical member pivotally connected to each of the first and second horizontal members via a third and fourth set of pivots; and
    plates of a high thermal conductivity material surrounding the movable vertical member, the first horizontal member and the second horizontal member,
    wherein the movable vertical member and at least one of the first and second horizontal members each comprise a composite member that comprises electrically conductive traces disposed on an insulator,
    wherein a continuous electrically conductive path extends from the electrically conductive traces of the vertical movable member to the vertical fixed member without the use of flexible wire leads, and
    wherein the entire balance is housed within an enclosure that is maintained at a constant uniform temperature.

14. The parallel guided balance of claim 13, further comprising:
    a holder assembly that includes sample and reference sensors that are configured for one of DSC and DTA measurements;
    wherein the holder assembly is rigidly affixed to the vertical movable member, and
    wherein the sample and reference sensors are each electrically conductively connected to respective conductive traces in the vertical fixed member via the conductive traces in the vertical movable member and the conductive traces in the at least one of the first and second horizontal members.

15. The parallel guided balance of claim 14, wherein at least one of the first and second horizontal members comprises a printed circuit board material that includes a set of electrically conductive traces.

16. The parallel guided balance of claim 13, wherein all the first, second, third and fourth sets of pivots are crossed-flexure pivots.

17. The parallel guided balance of claim 16, wherein at least one of the first set of pivots and the second set of pivots is an electrically conducting pivot, and
    wherein at least one of the third set of pivots and the fourth set of pivots is an electrically conducting pivot.

18. The parallel guided balance of claim 17, wherein the holder assembly comprises one of a vertical holder and a horizontal holder.

19. An instrument, comprising:
    a holder assembly that includes a means for conducting electrical signals from the holder assembly;
    a first composite balance member mechanically coupled to the holder assembly;
    a second composite balance member, wherein plates of a high thermal conductivity material surround the first and second composite members; and
    a coupling means,
    wherein the coupling means comprises:
    pivot means for pivotally connecting the first composite balance member to the second composite balance member, and
    a continuous electrically conductive path between the conductive means on the first composite balance member and the conductive means on the second composite balance member;
    wherein the composite balance members, the pivot means, and the electrically conductive path are housed within a temperature-regulated enclosure.

20. The instrument of claim 19, wherein at least one of the first and second composite balance members comprises a printed circuit board material.

21. The instrument of claim 19, wherein the pivot means is a crossed-flexure pivot.

22. The instrument of claim 19, wherein the instrument comprises a linear motor and a position sensor.

23. The instrument of claim 22, wherein the linear motor and the position sensor are housed within the temperature-regulated enclosure.

24. A simultaneous thermal analysis instrument comprising:
(a) a parallel guided balance comprising:
a stationary structure supporting a fixed vertical member and a meter movement comprising a linear motor and a position sensor;
a first set of flexures pivotally attaching an upper horizontal member to the stationary structure;
a second set of flexures pivotally attaching a lower horizontal member to the fixed structure;
a third set of flexures pivotally attaching the upper horizontal member to a movable vertical member;
a fourth set of flexures pivotally attaching the lower horizontal member to the movable vertical member;
a holder assembly rigidly attached to the movable vertical member,
wherein the upper and lower horizontal members have matching lengths and matching thermal expansion coefficients, wherein the movable vertical member is constrained to move such that its orientation remains parallel to the fixed vertical member, and wherein plates of a high thermal conductivity material surround the movable vertical member and the upper and lower horizontal members; and
(b) a DTA or DSC instrument comprising:
sensors for measuring the differential heat flow to a sample holder in the holder assembly with respect to the heat flow to a reference holder in the holder assembly;
conductive traces on one of the upper or lower horizontal members for conducting electrical signals from the sensors to the fixed vertical member,
wherein the flexures attaching the one of the upper or lower horizontal member to the movable vertical member and to the fixed vertical member are conductive flexures;
wherein the instrument is housed within a temperature-regulated enclosure.

25. The simultaneous thermal analysis instrument of claim 24, wherein the horizontal members are manufactured from printed circuit board material.

26. The simultaneous thermal analysis instrument of claim 24, wherein the high thermal conductivity material is one of copper, oxygen-free copper, silver and aluminum.

27. The simultaneous thermal analysis instrument of claim 24, wherein the upper and lower horizontal members are isosceles triangles, having their bases pivotally attached to the fixed vertical member and their apexes pivotally attached to the movable vertical member.

* * * * *